United States Patent
von Berg et al.

(10) Patent No.: US 10,360,680 B2
(45) Date of Patent: *Jul. 23, 2019

(54) VISUALIZATION OF PROJECTION X-RAY IMAGE

(71) Applicant: KONINKLIJKE PHILIPS N.V., Eindhoven (NL)

(72) Inventors: Jens von Berg, Hamburg (DE); Stewart Young, Hamburg (DE); Prasad Adhikarath Valappil, Bangalore (IN)

(73) Assignee: KONINKLIJKE PHILIPS N.V.

(*) Notice: Subject to any disclaimer, the term of this patent is extended or adjusted under 35 U.S.C. 154(b) by 1 day.

This patent is subject to a terminal disclaimer.

(21) Appl. No.: 15/884,668

(22) Filed: Jan. 31, 2018

(65) Prior Publication Data
US 2018/0182097 A1 Jun. 28, 2018

Related U.S. Application Data

(63) Continuation of application No. 15/255,249, filed on Sep. 2, 2016, now Pat. No. 9,892,509.

(30) Foreign Application Priority Data

Sep. 29, 2015 (EP) ..................................... 15187252

(51) Int. Cl.
*G06K 9/00* (2006.01)
*G06T 7/00* (2017.01)
(Continued)

(52) U.S. Cl.
CPC ............ *G06T 7/0012* (2013.01); *A61B 6/461* (2013.01); *A61B 6/463* (2013.01); *A61B 6/467* (2013.01);
(Continued)

(58) Field of Classification Search
None
See application file for complete search history.

(56) References Cited

U.S. PATENT DOCUMENTS 7,567,724 B2 7/2009 Gomi et al.
7,627,159 B2 12/2009 Kilary et al.
(Continued)

OTHER PUBLICATIONS

Al Okashi, O. et al.,"Automatic ribs segmentation and counting from mouse X-ray images", Conference Paper, Conference Medical Image Understanding and Anaylysis 2014, London, UK.
(Continued)

*Primary Examiner* — Atiba O Fitzpatrick
(74) *Attorney, Agent, or Firm* — Larry Liberchuk

(57) ABSTRACT

A system and method are provided for obtaining an improved visualization of bone objects comprised in a projection X-ray image. The projection X-ray image comprises bone objects which at least in part overlap. According to the system and method, a number of the bone objects are delineated by a contour, thereby obtaining a number of delineated bone objects. For each of the number of delineated bone object, a bone suppression technique is applied to the image to obtain respective bone image data individually showing the respective delineated bone object while suppressing shadows of obstructing objects. The bone image data generated for each of the number of delineated bone objects is used to generate an output image in which the bone objects do not overlap. An advantage of the system and method is that a non-overlapping, shadow-suppressed, presentation of the bone objects may be created from an X-ray image which was obtained by projectional radiography.

19 Claims, 6 Drawing Sheets

(51) Int. Cl.
    *A61B 6/00*     (2006.01)
    *G06T 5/00*     (2006.01)

(52) U.S. Cl.
    CPC ............ *A61B 6/505* (2013.01); *A61B 6/5205* (2013.01); *A61B 6/5252* (2013.01); *G06T 5/005* (2013.01); *G06T 2207/10116* (2013.01); *G06T 2207/20092* (2013.01); *G06T 2207/30008* (2013.01)

(56) References Cited

U.S. PATENT DOCUMENTS

| | | | |
|---|---|---|---|
| 7,697,739 | B2 | 4/2010 | Sakaida |
| 8,903,153 | B2 | 12/2014 | Von Berg et al. |
| 2005/0100208 | A1 | 5/2005 | Suzuki et al. |
| 2009/0087070 | A1 | 4/2009 | Slabaugh et al. |
| 2009/0214099 | A1 | 8/2009 | Merlet |
| 2012/0257810 | A1 | 10/2012 | Bon Berg et al. |
| 2013/0070996 | A1 | 3/2013 | Liu et al. |
| 2013/0101197 | A1 | 4/2013 | Kaftan et al. |
| 2014/0079309 | A1 | 3/2014 | Huo et al. |
| 2014/0140479 | A1 | 5/2014 | Wang et al. |
| 2014/0140603 | A1 | 5/2014 | Huo et al. |
| 2014/0376798 | A1 | 12/2014 | La Pietra et al. |
| 2016/0125595 | A1 | 5/2016 | Silbert et al. |
| 2017/0116730 | A1 | 4/2017 | Yamanaka |

OTHER PUBLICATIONS

Simko, G. et al., "Elimination of clavicle shadows to help automatic lung nodule detection on chest radiographs", 4th European Conference of the International Federation for Medical and Biological Engineering: ECIFMBE 2008 Nov. 23-27, 2008 Antwerp, Belgium, Springer, Berlin, DE, vol. 22, No. 7, Jan. 1, 2009, pp. 488-491.

Rasheed, T. et al., "Rib suppression in frontal chest radiographs: A blind source separation approach", Signal Processing and its Applications, 2007. ISSPA 2007, 9th International Symposium on, IEEE, Piscataway, NJ, USA, Feb. 12, 2007, pp. 1-4.

Zhao, H., "Enhanced Lung Cancer Detection in Temporal substraction chect radiography using directional edge filtering techniques", Proceedings of SPIE, USA, vol. 4684, Jan. 1, 2002, pp. 1-6.

Suzuki, et al., "Suppression of the contrast of ribs in chest radiographs by means of massive training artificial neural network", Proceedings of SPIE, vol. 5370, May 12, 2004, pp. 1108-1119.

VISUALIZATION OF PROJECTION X-RAY IMAGE

CROSS-REFERENCE TO RELATED APPLICATIONS

This application is a continuation of U.S. application Ser. No. 15/255,249, filed on Sep. 2, 2016, which claims the benefit of European Patent Application No. 15187252.0, filed on Sep. 29, 2015. These applications are hereby incorporated by reference herein.

FIELD OF THE INVENTION

The invention relates to a system and a method for processing a projection X-ray image comprising bone objects which at least in part overlap.

The invention further relates to a workstation and imaging apparatus comprising the system. The invention further relates to a computer program product comprising instructions for causing a processor system to perform the method.

BACKGROUND OF THE INVENTION

The reading of projection X-ray images, also referred to as radiographs, is a tedious and exhausting procedure as they typically come in batches and time pressure is high. Radiologists are trained to visually follow a certain path in their reading in order not to oversee details that may turn out diagnostically relevant. For example, for a posterior-anterior chest radiograph, most attention is directed to analyze the lung fields for so as to determine soft tissue findings, and to the cardio-vascular system. But also bone-related findings may be of importance, examples of which include metastases, cysts, or small fractures.

In the example of the posterior-anterior chest radiograph, in order to rule out bone lesions during the image reading, each rib has to be followed along its extent from the spine via the lateral turn point to the anterior tip of the rib. In the posterior-anterior chest radiograph, this path describes a curve. Along this curve, a number of other structures are crossing that are overlaid in the projection image. These are mainly other neighboring ribs, but also clavicles, the lung field border, the shadow of the breast, the heart shadow, and others. These overlaid structures visually distract the reader from following the rib and identifying any lesions associated with the rib. It is noted that similar problems occur also in other types of radiographs which involve other types of bone objects than ribs.

It is known to unfold the rib cage from a 3D computed tomography (CT) volume into a 2D image, for example from U.S. 2013/070996 A1. It is said that the ability to unfold the CT volume data from 3D to 2D may help doctors to locate rib lesions more easily and accurately, since small lesions are typically difficult to identify and locate in the 3D CT volume, but easier to locate in a corresponding 2D unfolded image. Similar techniques appear also to be known from U.S. 2013/101197 A1, citing WO 2006/050102.

Disadvantageously, the above identified 'rib unfolding' method is only applicable to 3D CT volume data and cannot be applied to projection X-ray images.

SUMMARY OF THE INVENTION

It would be advantageous to have a system or method for providing an improved visualization of the bone objects comprised in a projection X-ray image.

A first aspect of the invention provides a system for processing a projection X-ray image comprising bone objects which at least in part overlap, the system comprising:
   an input interface for accessing the X-ray image;
   a processor for processing the X-ray image by:
      i) delineating a number of the bone objects by a contour, thereby obtaining a number of delineated bone objects;
      ii) for each of the number of delineated bone object, applying a bone suppression technique to the image to obtain respective bone image data individually showing the respective delineated bone object while suppressing shadows of obstructing objects; and
      iii) using the bone image data generated for each of the number of delineated bone objects to generate an output image in which the bone objects do not overlap.

A further aspect of the invention provides a workstation or imaging apparatus comprising the system.

A further aspect of the invention provides a method for processing a projection X-ray image comprising bone objects which at least in part overlap, the method comprising:
   accessing the X-ray image;
   processing the X-ray image by:
      i) delineating a number of the bone objects by a contour, thereby obtaining a number of delineated bone objects;
      ii) for each of the number of delineated bone object, applying a bone suppression technique to the image to obtain respective bone image data individually showing the respective delineated bone object while suppressing shadows of obstructing objects; and
      iii) using the bone image data generated for each of the number of delineated bone objects to generate an output image in which the bone objects do not overlap.

A further aspect of the invention provides a computer program product comprising instructions for causing a processor system to perform the method.

The above measures involve accessing the image data of a projection X-ray image, e.g., as obtained by projectional radiography. The projection X-ray image is thus typically a 2D image. Said X-ray image comprises two or more bones, or bone parts, henceforth commonly referred to as bone objects, which at least in part overlap in the X-ray image. As such, unlike a 3D CT Volume, the X-ray image comprises a superposition of shadows from different objects overlaid with each other. Therefore, the X-ray image comprises at least a shadow caused by a bone object. The X-ray image may also comprise shadows from multiple bone objects, and/or other types of shadows, e.g., from soft tissue.

A number of the bone objects is delineated by a contour, e.g., in a manner known per se from the field of medical image segmentation. As a result, an outline of each of said bone objects is determined, thereby identifying their location and shape in the image.

To each of the delineated bone objects, a bone suppression technique is applied. Bone suppression techniques are known per se, e.g., from EP 2,517,174, as well as from other publications, and involve using image processing to suppress shadows of obstructing objects in an image. Such shadows include, but are not limited to those of bone objects. It is noted that bone suppression techniques may be used to estimate an image of the bones, i.e., a "bone image", from an X-ray image, and thereby represent an alternative to dual energy X-ray acquisition systems. Such use is also referred to as Bone Suppression Imaging (BSI). By applying the bone suppressing technique to each of the delineated bone objects, image data is obtained showing each bone object individually, with shadows of obstructing objects, including those caused by overlapping bone objects, being suppressed.

An output image is generated using the image data of each of the delineated bone objects, as obtained from the bone suppression technique. In generating the output image, the image data of said bone objects is combined in such a manner so that the bone objects, which were processed in the claimed manner, do not overlap in the output image, e.g., by being shown apart from each other. It is noted that this non-overlapping may apply to the bone objects which are processed in the claimed manner, but that there may exist bone objects in the image which are not processed as such and thus may still overlap.

The above measures have as effect that an output image is obtained in which the processed bone objects do not overlap. Namely, by applying a bone suppression technique, an individual presentation of each bone object can be obtained, in the form of corresponding image data for each bone object, which is largely free of shadows of obstructing objects including those of other bone objects. By combining these individual presentations into a single image again, the output image may be generated. Accordingly, an improved visualization of the bone objects comprised in an X-ray image is obtained.

Optionally, the processor is configured for, before generating the output image, applying a geometric transformation to the bone image data of each bone object to geometrically transform the respective bone object. Geometrically transforming a bone object may aid a clinician in reading the bone object in the output image. Additionally or alternatively, geometrically transforming a bone object may facilitate combining the individual presentations of the bone objects into the output image.

Optionally, the geometric transformation is configured to reduce a curvature of the respective bone object. This allows curved bone objects, such as ribs, to be partially or entirely reduced in their curvature, i.e., straightened, which may improve their readability by a clinician and/or their combinability into a single output image.

Optionally, said delineating by a contour provides a centerline of the respective bone object, and the geometric transformation is configured to straighten the centerline. When desiring to straighten a curved bone object, a centerline of the bone object is well suited for using as target object in the straightening.

Optionally, the processor is configured for generating the output image based on composition data, the composition data defining a relative positioning of the number of delineated bone objects in the output image. The composition data may thus define how the individual presentations of the bone objects are to be combined in the output image.

Optionally, the composition data defines a tiling of the number of delineated bone objects which reduces non-bone space between the number of delineated bone objects while preserving their relative anatomical positioning. It may be desirable for maintaining readability of the output image by a clinician to maintain the relative anatomical positioning of the bone objects in the output image, while at the same time reducing non-bone space between bone objects. For that purpose, composition data is provided which is used to generate the output image from the individual presentations of the bone objects.

Optionally, the system further comprises a display output for outputting the output image to a display, wherein the display output is further configured for outputting the X-ray image simultaneously with the output image. Showing the X-ray image simultaneously with the output image may allow a clinician to quickly jump back and forth between both images, e.g., to verify a pathological finding from the output image in the X-ray image. Optionally, the system further comprises a user interaction subsystem comprising a user input interface and the display output, wherein the user interaction subsystem is configured for:

enabling the user to interactively position a display marker in a first one of a group of: the X-ray image and the output image, and displaying a corresponding display marker in a second one of the group. The simultaneously displayed X-ray image and output image are provided with linked display markers, such as two linked pointers or cross-hairs. This may facilitate the simultaneous or alternating reading of the displayed images by a clinician.

Optionally, the user interaction subsystem is configured for establishing a position of the corresponding display marker based on the geometric transformation of each respective bone object. By taking the geometric transformations into account by which the individual presentations of the bone objects were obtained, the display markers may be accurately linked in that a display marker in the X-ray image and a corresponding display marker in the output image may be displayed at anatomical corresponding positions.

Optionally, the user interaction subsystem is configured for establishing a position of the corresponding display marker further based on the composition data. It will be appreciated by those skilled in the art that two or more of the above-mentioned embodiments, implementations, and/or optional aspects of the invention may be combined in any way deemed useful.

Modifications and variations of the imaging apparatus, the workstation, the method, and/or the computer program product, which correspond to the described modifications and variations of the system, can be carried out by a person skilled in the art on the basis of the present description.

BRIEF DESCRIPTION OF THE DRAWINGS

These and other aspects of the invention will be apparent from and elucidated further with reference to the embodiments described by way of example in the following description and with reference to the accompanying drawings, in which.

It should be noted that the figures are purely diagrammatic and not drawn to scale. In the Figures, elements which correspond to elements already described may have the same reference numerals.

LIST OF REFERENCE NUMBERS

Figure 1:
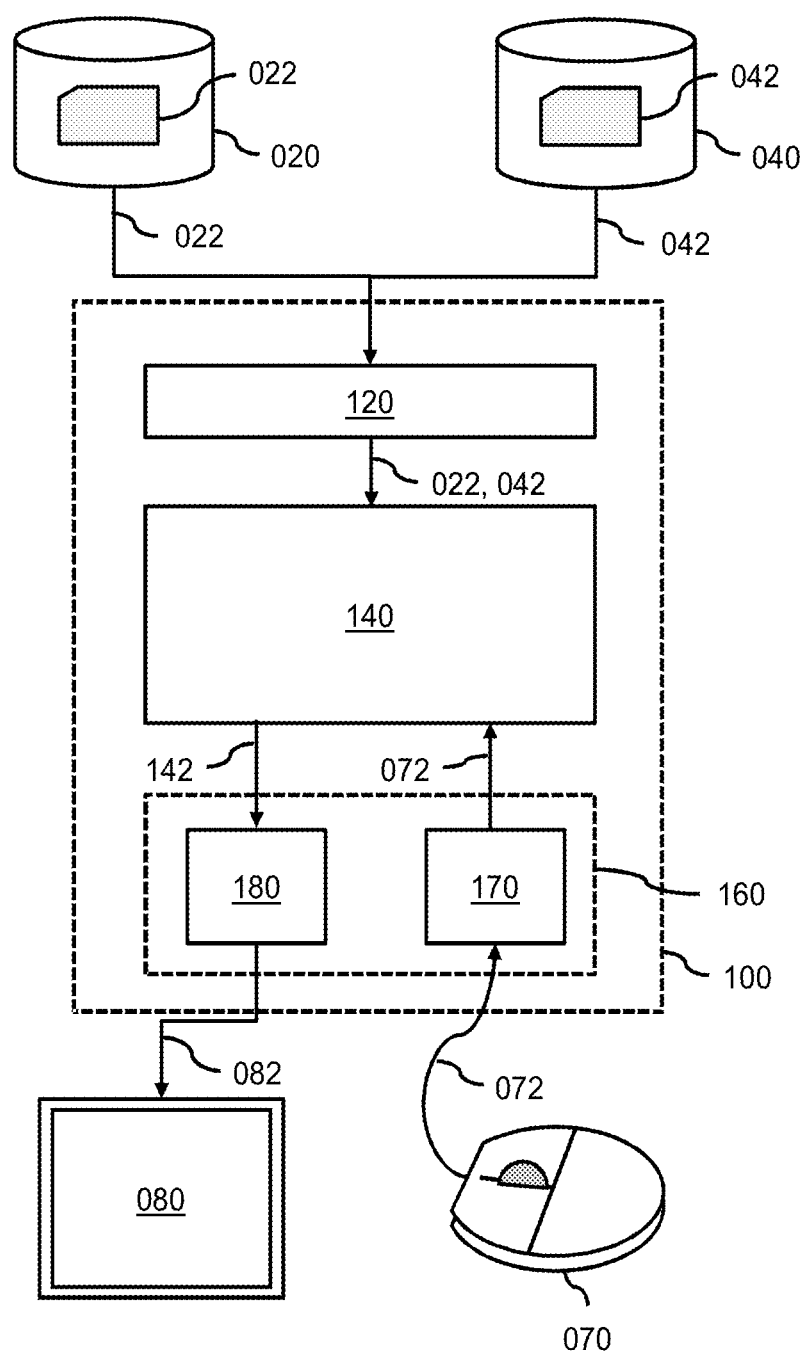
FIG. 1 shows a system for processing an X-ray image, including optional aspects such as a user interactions subsystem.

The following list of reference numbers is provided for facilitating the interpretation of the drawings and shall not be construed as limiting the claims.
020 image repository
022 image data of X-ray image
040 auxiliary data storage
042 auxiliary data
070 user input device
072 user input data
080 display
082 display data
100 system for processing X-ray image
120 input interface
140 processor
142 output image
160 user interface subsystem
170 user input interface
180 display output
200, 202 X-ray image
204 X-ray image showing delineated bone objects
210 bone image obtained by bone suppression imaging
220 soft tissue image obtained by bone suppression imaging
230 single bone image obtained by bone suppression
240 output image showing tiling of bone objects
250, 252 plurality of bone objects
260 plurality of delineated bone objects
262 delineated bone object
270 bone object after bone suppression
272 straightened bone object
300 method for processing X-ray image
310 accessing X-ray image
320 delineating bone objects
330 applying bone suppression technique
340 generating output image
370 computer readable medium
380 instructions stored as non-transient data

DETAILED DESCRIPTION OF EMBODIMENTS

FIG. 1 shows a system 100 for processing a projection X-ray image. The system 100 comprises an input interface 120 for accessing image data 022 representing the X-ray image. In the example of FIG. 1, the input interface 120 is shown to be connected to an external image repository 020 which comprises the image data 022 of the X-ray image. For example, the image repository 020 may be constituted by, or be part of, a Picture Archiving and Communication System (PACS) of a Hospital Information System (HIS) to which the system 100 may be connected or comprised in. Accordingly, the system 100 may obtain access to the image data 022 of the X-ray image via the HIS. Alternatively, the image data 022 may be accessed from an internal data storage of the system 100. In general, the input interface 120 may take various forms, such as a network interface to a local or wide area network, e.g., the Internet, a storage interface to an internal or external data storage, etc.

The system 100 further comprises a processor 140 which is configured for processing the X-ray image and for generating an output image. For that purpose, the processor 140 is shown to receive the image data 022 of the X-ray image from the input interface 120, and to output image data 142 of the generated output image.

The X-ray image comprises bone objects which at least in part overlap. During an operation of the system 100, the processor 140 may process the X-ray image by i) delineating a number of the bone objects by a contour, thereby obtaining a number of delineated bone objects; ii) for each of the number of delineated bone object, applying a bone suppression technique to the image to obtain respective bone image data individually showing the respective delineated bone object while suppressing shadows of obstructing objects; and iii) using the bone image data generated for each of the number of delineated bone objects to generate the output image in which the bone objects do not overlap. It is noted that various operations of the system 100, including various optional aspects thereof, will be explained in more detail with reference to FIGS. 2A-4.

It is further noted that FIG. 1 shows some of these optional aspects of the system 100. Namely, the input interface 120 is shown to be configured to access auxiliary data 042 on an auxiliary data storage 040. Examples of auxiliary data 042 include composition data and reference data. Furthermore, the system 100 is shown to comprise a user interface subsystem 160 which comprises a user input interface 170 for receiving user input data 072 from a user device 070 operable by the user. The user device 070 may take various forms, including but not limited to a computer mouse 070, touch screen, keyboard, etc. The user input interface 170 may be of a type which corresponds to the type of user device 070, i.e., it may be a thereto corresponding user device interface. The user interface subsystem 160 is further shown to comprise a display output 180 for providing display data 082 to a display 080. For example, the display data may comprise the output image 142.

The system 100 may be embodied as, or in, a single device or apparatus, such as a workstation or imaging apparatus. The device or apparatus may comprise one or more microprocessors which execute appropriate software. The software may have been downloaded and/or stored in a corresponding memory, e.g., a volatile memory such as RAM or a non-volatile memory such as Flash. Alternatively, the functional units of the system may be implemented in the device or apparatus in the form of programmable logic, e.g., as a Field-Programmable Gate Array (FPGA). In general, each functional unit of the system may be implemented in the form of a circuit. It is noted that the system 100 may also be implemented in a distributed manner, e.g., involving different devices or apparatuses. For example, the distribution may be in accordance with a client-server model.

The following examples relate to chest radiography. It will be appreciated, however, that this is a non-limiting example, and that the invention as claimed is equally applicable to other types of radiographs in which bone objects at least in part overlap. For example, the invention as claimed may be used to obtain a presentation of the bones of a body imaged by projection X-ray in an arbitrary pose in which the bones are ordered canonically while avoiding bone crossings. For example, such a presentation may place the abdomen in the center of the output image and arranged the bones of the limbs around it, e.g., with those of the fingers and/or toes being positioned furthest from the abdomen.

Chest radiography is one of the most commonly performed clinical examinations, and plays an important role in detecting and diagnosing many diseases of the thoracic anatomy. While the osseous anatomical structures (bones) are typically highly contrasted in radiographs of the chest, due to their higher X-ray absorption with respect to the surrounding soft-tissue, a reader's attention is nevertheless often focused upon the other anatomical features. Thus, bones are often considered as disturbing overlaying structures (e.g., when lung cancer nodules are of interest). Relevant clinical findings in the bones such as (partial-) fractures or calcifications of the bones, or metastatic bone lesions, may thus be overlooked. Recently, significant attention has been placed upon improving the visualization and detection in chest x-rays of soft-tissue lesions such as solitary pulmonary nodules. For example, dual-energy subtraction (DES) imaging has been proposed, whereby a weighted subtraction of two posteroanterior (PA) projection radiographs is collected using different X-ray energies (typically 120 and 60 kV) to estimate the contribution of the bones in the image, which is then subtracted from the original image in order to generate a "soft tissue image", thereby simplifying the resulting interpretation task. Although the primary benefit of DES is to improve visualization and detection of soft tissue lesions, the technique also enables dedicated visualization of the bones and thereby also supports bone lesions detection.

Bone Suppression Imaging (BSI) has been proposed as an alternative to DES imaging which does not involve the use of dedicated hardware and multiple acquisitions. BSI may involve pattern recognition algorithms which estimate the "bones image" using a single PA projection radiograph. Following such estimation, the bones are then subtracted to obtain a "soft image" analogously to DES imaging. Several approaches have been proposed, which can be distinguished as either implicit approaches, where bones are implicitly represented, e.g., as the output response of an artificial neural network (ANN), as described by, e.g., Suzuki et al in "Suppression of the Contrast of Ribs in Chest Radiographs by Means of Massive Training Artificial Neural Network", or explicit approaches, where contours of the individual bone are explicitly estimated, as described in, e.g., European Patent 2,517,174.

Figure 2A:
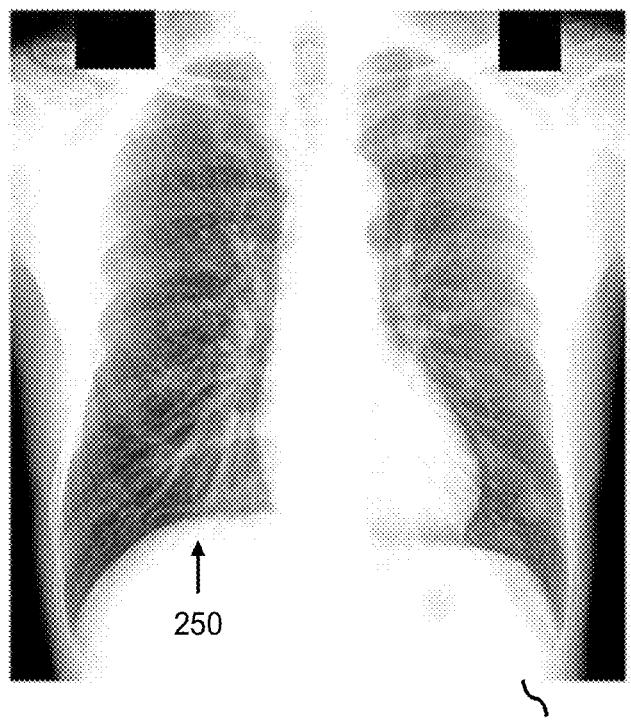
FIG. 2A shows an X-ray image in the form of a posterior-anterior chest radiograph, the X-ray image showing a plurality of ribs.
Figure 2B:
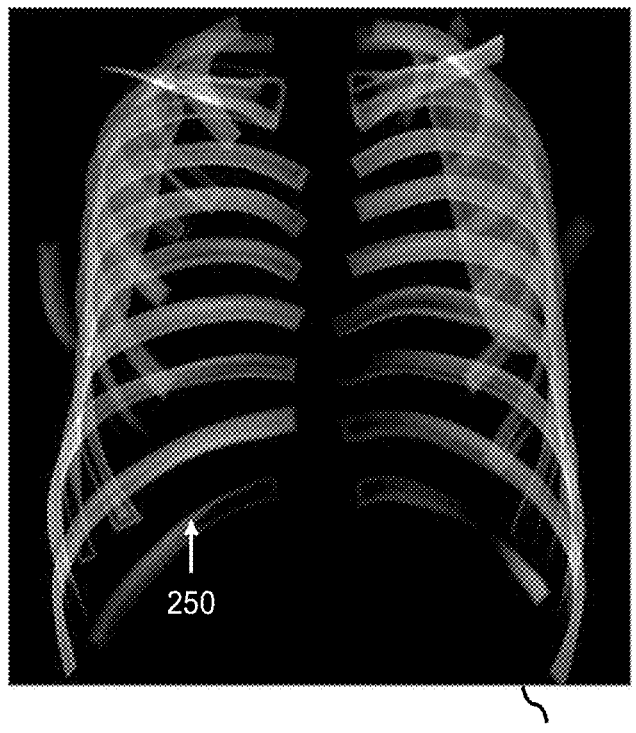
FIG. 2B shows a bone image obtained by bone suppression imaging.
Figure 2C:
FIG. 2C shows a soft-tissue image obtained by bone suppression imaging.

FIGS. 2A-2C illustrate such bone suppression imaging. Namely, FIG. 2A shows an X-ray image 200 in the form of a posterior-anterior chest radiograph. Accordingly, the X-ray image 200 shows a plurality of ribs 250. Due to their curvature, the ribs 250 in part overlap in the X-ray image. FIG. 2B shows the bone image 210 obtained by bone suppression imaging, whereas FIG. 2C shows a soft-tissue image 220 obtained by bone suppression imaging, namely by subtracting the bone image of FIG. 2B from the X-ray image of FIG. 2A.

Figure 3A:
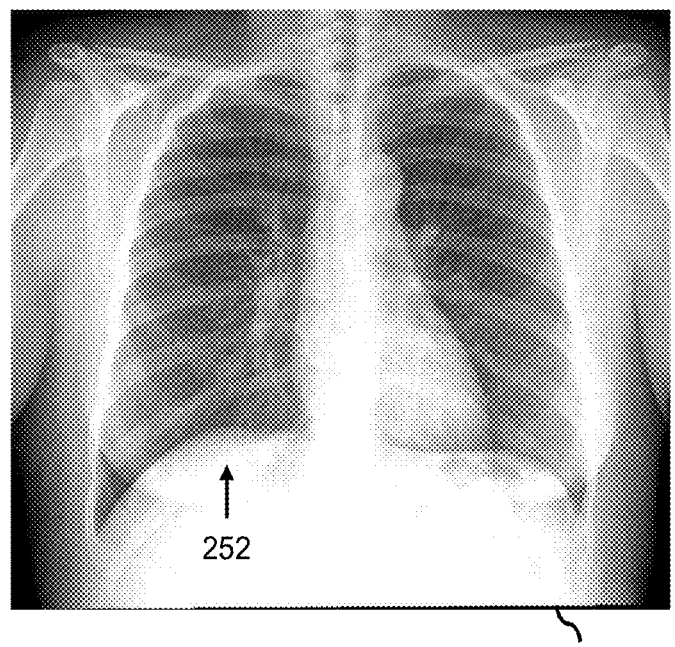
FIG. 3A shows an X-ray image in the form of another posterior-anterior chest radiograph, the X-ray image showing a plurality of ribs.
Figure 3B:
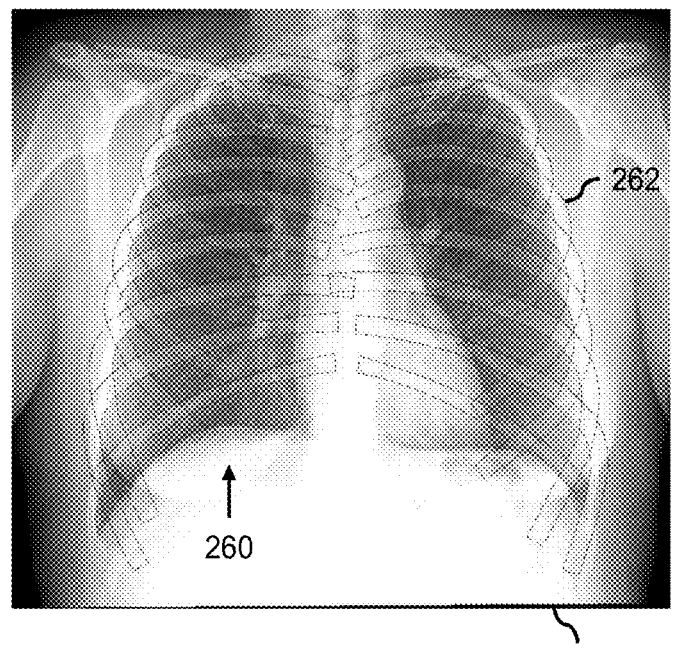
FIG. 3B shows the X-ray image with the ribs delineated by contours.
Figure 3C:
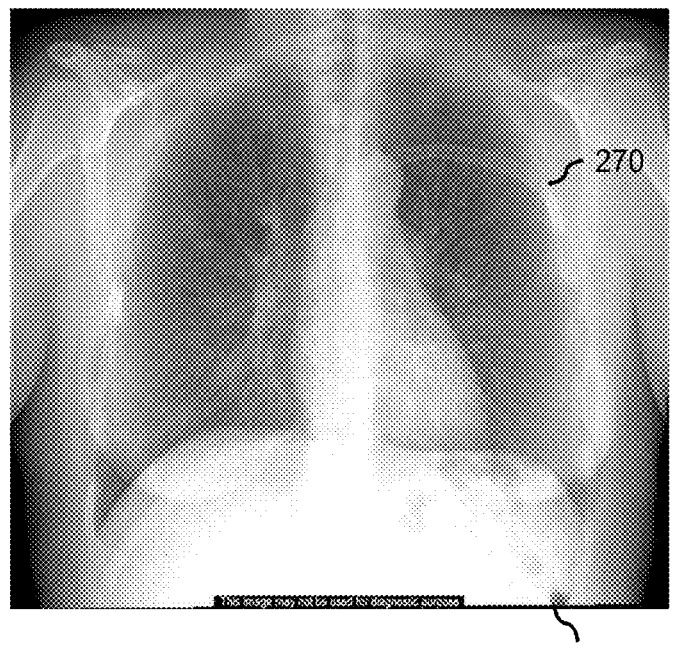
FIG. 3C shows a single bone image obtained by bone suppression.

The inventors have recognized that the bone suppression techniques used in explicit bone suppression imaging may also be used to obtain, from an input X-ray image in which bone objects at least in part overlap, an output image in which all, or at least some of the bone objects, do not overlap anymore. An example of such an input X-ray image 202 is shown in FIG. 3A, again showing a posterior-anterior chest radiograph comprising a plurality of ribs 252. A number of the ribs 252, e.g., all or a subset thereof, may be delineated by a contour in a manner known per se from the field of medical image segmentation. As such, a number of delineated ribs may be obtained, as illustrated in the image 204 of FIG. 3B which shows contours 260 overlaying the ribs. For each of the number of delineated ribs, a bone suppression technique may be applied to the image 204, yielding bone image data which individually shows the respective delineated bone object while suppressing shadows of obstructing object. FIG. 3C shows a bone image 230 obtained from such processing, namely the applying of the bone suppression technique to the 5$^{th}$ left rib (262 in FIG. 3B). It can be seen that bone image 230 shows the 5$^{th}$ left rib 270 in isolation as other ribs are omitted, while also suppressing shadows of other ribs and/or other objects. A similar bone image 230 as in FIG. 3C may be obtained for each of the delineated ribs. These bone images may then be combined to generate an output image in which the bone objects do not overlap.

Figure 4:
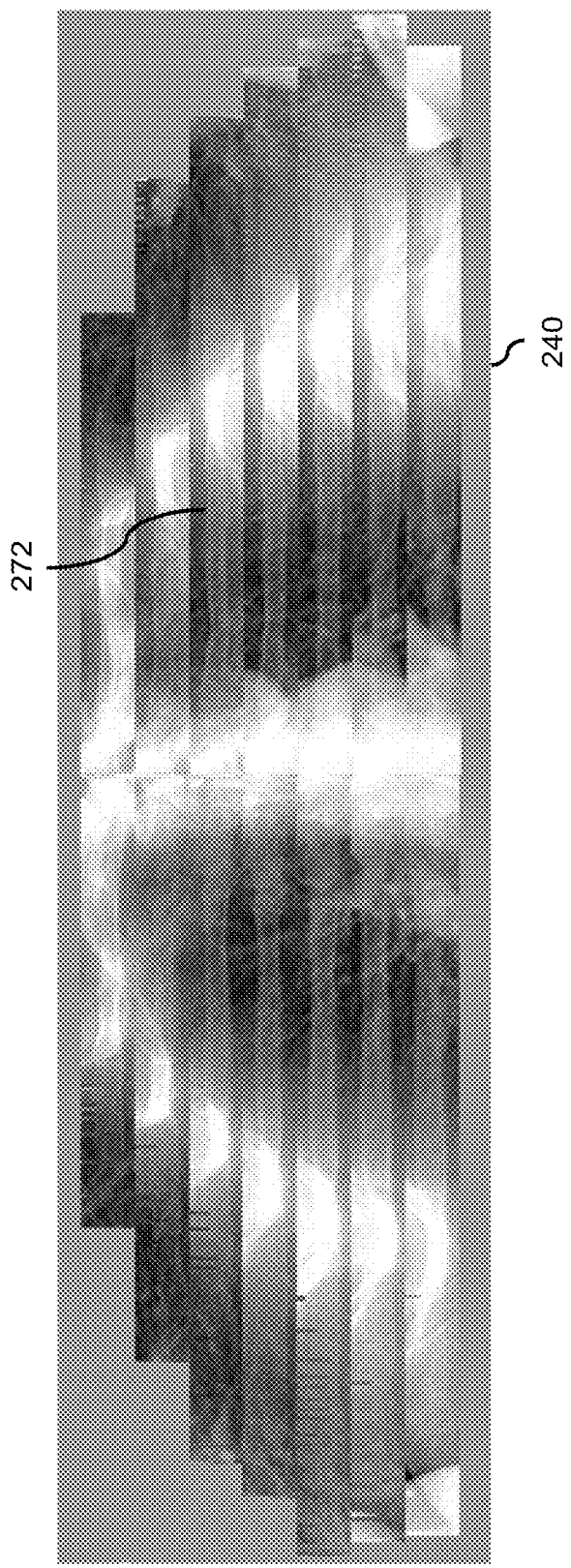
FIG. 4 shows an output image of the system an method.

FIG. 4 shows an example of such an output image 240. In this example, the ribs are shown to be straightened, e.g., as shown by a straightened left rib 272, and presented in a tiled manner such that non-bone space between the ribs is reduced while preserving their relative anatomical positioning. As such, a presentation of ribs is obtained which visually resembles the straightening of U.S. 2013/070996 A1, albeit being obtained in a different manner and from a projection X-ray image instead of from a 3D CT volume.

It is noted that in order to obtain the presentation of FIG. 4, as well as other types of presentations in which the bone objects do not overlap, the processor may be configured for, before generating the output image, applying a geometric transformation to the bone image data of each bone object to geometrically transform the respective bone object. Such a geometric transformation may be an 'elastic' or 'non-rigid' transformation, as known per se from the field of image registration, and may be defined by a set of parameters representing the transformation. For example, the geometric transformation may reduce a curvature of the respective bone object. As in the example of FIG. 4, the curvature may be reduced substantially entirely, in that the bone object may be straightened. For that purpose, a centerline of the respective bone object may be used, which may be detected as part of, or following, a delineation of the bone object. It is noted that the tiling, or other type of composition of the bone image data of the bone objects, may be defined by composition data which may be accessed by the input interface. It is further noted that although FIG. 3C showed the bone suppression technique yielding a complete image for the bone object to which it is applied, i.e., the 5$^{th}$ left rib, it may suffice to only obtain bone image data showing the bone object with no or a only limited surroundings. For example, such bone image data may then, after geometric transformation, directly be tiled to obtain the output image.

With further reference to the user interaction subsystem shown in FIG. 1, it is noted that the X-ray image may be displayed simultaneously with the output image, e.g., in a side-by-side or picture-in-picture arrangement. The user interaction subsystem may be further configured for enabling the user to interactively position a display marker on the display. If the display marker is positioned in either the input X-ray image or the output image, i.e., in a 'first' image', the system may display a corresponding display marker in the other 'second' image. The display marker in the second image may be positioned such that it mimics the anatomical position of the display marker in the first image. For example, if the display marker is positioned in the X-ray image on the 5$^{th}$ left rib, the system may be configured to display a corresponding display marker in the output image on the 5$^{th}$ left rib. To establish the corresponding anatomical position, the system may use the geometric transformation of each respective bone object and/or the composition data, which are both indicative of correspondences between image data of the X-ray image and the output image. It is noted that, alternatively, the corresponding anatomical position may be established by an image registration between the X-ray image and the output image, as known per se from the field of image registration, which would also be indicative of these correspondences.

It will be further appreciated that the bone image data obtained by the system and method may further be used for automatic detection of abnormalities which may be present in the bone objects. Such abnormalities include, but are not limited to, metastatic bone lesions and fractures. Namely, the bone image data of a delineated bone object may be compared to a typical appearance of the bone in the image(s) of healthy subjects. The explicit representation of the bone contours enables comparison of anatomical locations to corresponding locations in healthy anatomies for which explicit representation of the bones is also available. For example, this enables comparison of image intensity deviations between healthy and abnormal tissues, as well as the use of more sophisticated analytical tools such as Computer Assisted Diagnosis, in short CAD, methods. Reference cases may be stored in a database of radiographs and associated annotations, together with information relating to the status of these radiographs as determined, for example, by visual inspection of these images by an expert in radiological interpretation. Further dedicated filtering of the image signal along and perpendicular to the central axis of the rib bones, as described in, e.g., European Patent 2,517,174, may also enable automated detection of abnormal pathological features such as hairline fractures, which otherwise might be overlooked.

Accordingly, for detecting abnormalities in the bone objects, the input interface may be further configured for accessing a reference contour and bone image data of a reference bone object, e.g., in the form of auxiliary data from an auxiliary data storage. The processor may be further configured for i) determining a correspondence between the bone image data of the reference bone object and the bone image data of at least one of the number of delineated bone objects based on a mapping of their respective contours; and ii) comparing the bone image data of the reference bone object and the bone image data of said delineated bone object to detect a pathological finding. With further reference to the example of a posterior-anterior chest radiograph, each rib may, after being delineated, be mapped to a common co-ordinate system by parameterizing the centerline of the rib. It is noted that locations on the posterior aspect of the bone begin at the spinous process, and continue until the lateral turning point at the border of the lung field projection. The bone then continues to the anterior aspect. The same bone from different patients, or alternatively the same bone from the same patient imaged at a different point in time, e.g. during treatment, may be mapped into the common co-ordinate system using said normalized parameterization of the centerline, which provides, by way of the mapping, correspondences between the bone image data of the delineated bone objects and the bone image data of the reference bone object. As such, image information from the same anatomical location may be compared to detect deviations, e.g., between the patient and a set of healthy patients, or to a different time-point in the same patient's medical record. For example, a range of acceptable intensity deviations at a given location might be determined, and only deviations greater than this acceptable variation would then be indicated to the user as being suspicious. This threshold for acceptable intensity deviations may be spatially variant. Fractures of the bone may be automatically detected by quantifying intensity edges with respect to the axial direction of the bone. Higher-level moments, such as a second order signal derivative, in the intensity distribution along this axis may also be observed in order to detect nodule-like shapes, or other abnormal deviations of the bone image data of a delineated bone object.

It will be appreciated that the system and method the bones of a body imaged by X-ray in an arbitrary pose to achieve a canonical ordered plot avoiding bone crossings of it with the abdomen in the center and the limbs arranged around it, fingers/toes spreading even further from the abdomen.

Figure 5:
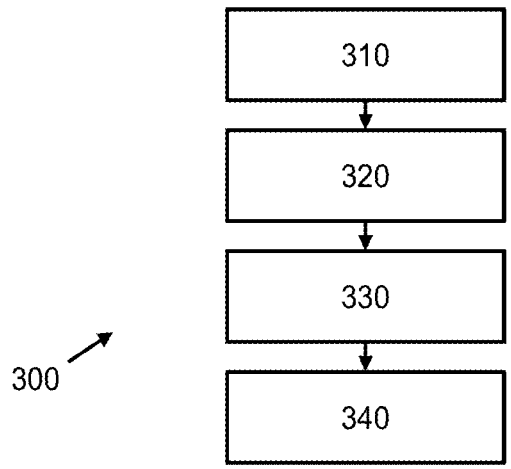
FIG. 5 shows a method for processing an X-ray image.

FIG. 5 shows a method 300 for processing an X-ray image comprising bone objects which at least in part overlap. It is noted that the method 300 may, but does not need to, correspond to an operation of the system 100 as described with reference to FIG. 1. The method 300 comprises, in an operation titled "ACCESSING X-RAY IMAGE", accessing 310 the X-ray image. The method 300 further comprises processing the X-ray image by, in an operation titled "DELINEATING BONE OBJECTS", delineating 320 a number of the bone objects by a contour, thereby obtaining a number of delineated bone objects. The method 300 further comprises, in an operation titled "APPLYING BONE SUPPRESSION TECHNIQUE", for each of the number of delineated bone object, applying 330 a bone suppression technique to the image to obtain respective bone image data individually showing the respective delineated bone object while suppressing shadows of obstructing objects. The method 300 further comprises, in an operation titled "GENERATING OUTPUT IMAGE", using the bone image data generated for each of the number of delineated bone objects to generate 340 an output image in which the bone objects do not overlap.

It will be appreciated that the above operation may be performed in any suitable order, e.g., consecutively, simultaneously, or a combination thereof, subject to, where applicable, a particular order being necessitated, e.g., by input/output relations.

Figure 6:
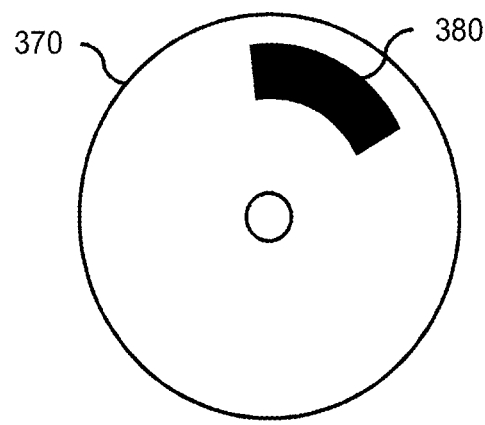
FIG. 6 shows a computer readable medium comprising instructions for causing a processor system to perform the method.

The method 300 may be implemented on a computer as a computer implemented method, as dedicated hardware, or as a combination of both. As also illustrated in FIG. 6, instructions for the computer, e.g., executable code, may be stored on a computer readable medium 370, e.g., in the form of a series 380 of machine readable physical marks and/or as a series of elements having different electrical, e.g., magnetic, or optical properties or values. The executable code may be stored in a transitory or non-transitory manner. Examples of computer readable mediums include memory devices, optical storage devices, integrated circuits, servers, online software, etc. FIG. 6 shows an optical disc 370.

It will be appreciated that, in accordance with the abstract of the present application, a system and method are provided for improved visualization of the bone objects comprised in a projection X-ray image. The projection X-ray image comprises bone objects which at least in part overlap. According to the system and method, a number of the bone objects are delineated by a contour, thereby obtaining a number of delineated bone objects. For each of the number of delineated bone object, a bone suppression technique is applied to the image to obtain respective bone image data individually showing the respective delineated bone object while suppressing shadows of obstructing objects. The bone image data generated for each of the number of delineated bone objects is used to generate an output image in which the bone objects do not overlap. An advantage of the system and method is that a non-overlapping, shadow-suppressed, presentation of the bone objects may be created from an X-ray image which was obtained by projectional radiography.

Examples, embodiments or optional features, whether indicated as non-limiting or not, are not to be understood as limiting the invention as claimed.

It will be appreciated that the invention also applies to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to the invention. It will also be appreciated that such a program may have many different architectural designs. For example, a program code implementing the functionality of the method or system according to the invention may be sub-divided into one or more sub-routines. Many different ways of distributing the functionality among these sub-routines will be apparent to the skilled person. The sub-routines may be stored together in one executable file to form a self-contained program. Such an executable file may comprise computer-executable instructions, for example, processor instructions and/or interpreter instructions (e.g. Java interpreter instructions). Alternatively, one or more or all of the sub-routines may be stored in at least one external library file and linked with a main program either statically or dynamically, e.g. at run-time. The main program contains at least one call to at least one of the sub-routines. The sub-routines may also comprise function calls to each other. An embodiment relating to a computer program product comprises computer-executable instructions corresponding to each processing stage of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of a computer program may be any entity or device capable of carrying the program. For example, the carrier may include a data storage, such as a ROM, for example, a CD ROM or a semiconductor ROM, or a magnetic recording medium, for example, a hard disk. Furthermore, the carrier may be a transmissible carrier such as an electric or optical signal, which may be conveyed via electric or optical cable or by radio or other means. When the program is embodied in such a signal, the carrier may be constituted by such a cable or other device or means. Alternatively, the carrier may be an integrated circuit in which the program is embedded, the integrated circuit being adapted to perform, or used in the performance of, the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or stages other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for processing a two-dimensional X-ray image comprising bone objects which at least in part overlap, the system comprising:
    an input interface for accessing the X-ray image;
    a display output;
    a user input interface; and
    a processor for processing the X-ray image by:
        delineating one or more of the bone objects to obtain one or more delineated bone objects;
        for each of the one or more delineated bone objects, applying an image processing technique to the image to obtain respective bone image data individually showing the respective delineated bone object while suppressing artifacts caused by other objects;
        using the bone image data generated for each of the one or more delineated bone objects to generate an output image in which at least some of the bone objects do not overlap;
    displaying the X-ray image on the display output simultaneously with the output image;
    enabling the user to operate the user input interface to interactively position a display marker in a first one of a group of: the X-ray image and the output image, and
    displaying a corresponding display marker in a second one of the group.

2. The system according to claim 1, wherein the processor is configured for, before generating the output image, applying a geometric transformation to the bone image data of each bone object to geometrically transform the respective bone object.

3. The system according to claim 2, wherein the geometric transformation is configured to reduce a curvature of the respective bone object.

4. The system according to claim 3, wherein said delineating provides a centerline of the respective bone object, and wherein the geometric transformation is configured to straighten the centerline.

5. The system according to claim 1, wherein the processor is configured for generating the output image based on composition data, the composition data defining a relative positioning of the one or more delineated bone objects in the output image.

6. The system according to claim 5, wherein the composition data defines a tiling of the one or more delineated bone objects which reduces non-bone space between the one or more delineated bone objects while preserving their relative anatomical positioning.

7. The system according to claim 2, wherein the user interaction subsystem is configured for establishing a position of the corresponding display marker based on the geometric transformation of each respective bone object.

8. The system according to claim 1, wherein:
    the input interface is further configured for accessing bone image data of a reference bone object; and
    the processor is further configured for:
        i) determining a correspondence between the bone image data of the reference bone object and the bone image data of at least one of the one or more delineated bone objects; and
        ii) comparing the bone image data of the reference bone object and the bone image data of said delineated bone object to detect a pathological finding.

9. The system according to claim 8, wherein the processor is configured for detecting the pathologic finding by:

determining a range of acceptable intensity deviations between the bone image data of the reference bone object and the bone image data of said delineated bone object; and indicating deviations greater than the acceptable intensity deviations.

10. The system according to claim 8, wherein the processor is configured for mapping at least part of the bone image data of the reference bone object and at least part of the bone image data of at least one of the one or more delineated bone object to a common coordinate system.

11. At least one non-transitory computer-readable medium comprising instructions that, in response to execution of the instructions by one or more processors, cause the one or more processors to process a two-dimensional X-ray image comprising bone objects which at least in part overlap with the following operations:

delineating one or more of the bone objects to obtain one or more delineated bone objects;

for each of the one or more delineated bone objects, applying an image processing technique to the image to obtain respective bone image data individually showing the respective delineated bone object while suppressing artifacts caused by other objects;

using the bone image data generated for each of the one or more delineated bone objects to generate an output image in which at least some of the bone objects do not overlap;

displaying the X-ray image on a display output device simultaneously with the output image;

enabling the user to interactively position a display marker in a first one of a group of: the X-ray image and the output image, and displaying a corresponding display marker in a second one of the group.

12. The at least one non-transitory computer-readable medium of claim 11, wherein further comprising instructions for, before generating the output image, applying a geometric transformation to the bone image data of each bone object to geometrically transform the respective bone object.

13. The at least one non-transitory computer-readable medium of claim 12, wherein the geometric transformation is configured to reduce a curvature of the respective bone object.

14. The at least one non-transitory computer-readable medium of claim 13, wherein said delineating provides a centerline of the respective bone object, and wherein the geometric transformation is configured to straighten the centerline.

15. The at least one non-transitory computer-readable medium of claim 11, further comprising instructions for generating the output image based on composition data, the composition data defining a relative positioning of the one or more delineated bone objects in the output image.

16. The at least one non-transitory computer-readable medium of claim 15, wherein the composition data defines a tiling of the one or more delineated bone objects which reduces non-bone space between the one or more delineated bone objects while preserving their relative anatomical positioning.

17. A method for processing a two-dimensional X-ray image comprising bone objects which at least in part overlap, the method comprising:

delineating one or more of the bone objects to obtain one or more delineated bone objects;

for each of the one or more delineated bone objects, applying an image processing technique to the image to obtain respective bone image data individually showing the respective delineated bone object while suppressing artifacts caused by other objects;

using the bone image data generated for each of the one or more delineated bone objects to generate an output image in which at least some of the bone objects do not overlap;

displaying the X-ray image on a display output device simultaneously with the output image;

enabling the user to interactively position a display marker in a first one of a group of: the X-ray image and the output image, and displaying a corresponding display marker in a second one of the group.

18. The method of claim 17, further comprising, before generating the output image, applying a geometric transformation to the bone image data of each bone object to geometrically transform the respective bone object.

19. The method of claim 18, wherein the geometric transformation is configured to reduce a curvature of the respective bone object.

* * * * *